United States Patent
Kerselaers et al.

(10) Patent No.: US 10,009,069 B2
(45) Date of Patent: Jun. 26, 2018

(54) WIRELESS POWER DELIVERY AND DATA LINK

(71) Applicant: NXP B.V., Eindhoven (NL)

(72) Inventors: Anthony Kerselaers, Herselt (BE); Liesbeth Gommë, Heverlee (BE); Steven Thoen, Leuven (BE); Johan Van Ginderdeuren, Leuven (BE)

(73) Assignee: NXP B.V., Eindhoven (NL)

( * ) Notice: Subject to any disclaimer, the term of this patent is extended or adjusted under 35 U.S.C. 154(b) by 0 days. days.

(21) Appl. No.: 14/569,024

(22) Filed: Dec. 12, 2014

(65) Prior Publication Data

US 2015/0318896 A1    Nov. 5, 2015

Related U.S. Application Data

(63) Continuation-in-part of application No. 14/270,013, filed on May 5, 2014, which is a continuation-in-part of application No. 14/302,791, filed on Jun. 12, 2014.

(51) Int. Cl.
*H04B 5/00* (2006.01)
*H02J 5/00* (2016.01)
(Continued)

(52) U.S. Cl.
CPC .......... *H04B 5/0037* (2013.01); *G08C 17/02* (2013.01); *G08C 17/04* (2013.01); *H02J 5/005* (2013.01);
(Continued)

(58) Field of Classification Search
CPC .. H04B 5/0037; H04B 13/005; H04B 5/0081; H04B 5/0031; H02J 5/005; H01Q 1/273; H04R 25/554; H04W 4/008
See application file for complete search history.

(56) References Cited

U.S. PATENT DOCUMENTS 3,766,476 A    10/1973  Silitch
4,334,315 A *  6/1982  Ono ................. H04B 1/385
                                        128/201.19
(Continued)

FOREIGN PATENT DOCUMENTS

CN    102013895 A    4/2011
CN    102570000 A    7/2012
(Continued)

OTHER PUBLICATIONS

T.G. Zimmerman, Personal Area Netwrks: Near-Field Intrabody Communication, IBM System Journal vol. 35, 1995, pp. 609-617.*
(Continued)

*Primary Examiner* — Fan Tsang
*Assistant Examiner* — Angelica M McKinney

(57) ABSTRACT

An electromagnetic induction wireless transceiver system including: a magnetic antenna; an electric antenna including first and second plates, the first plate being connectable to a body; and a power driver configured to produce a modulating signal used to drive the magnetic antenna and the electric antenna to produce electromagnetic induction fields, wherein the transceiver when connected to a body in a first location is configured to transmit power to a second electromagnetic induction wireless transceiver connected to a second location a distance from the first location, wherein the first and second locations are connected through magnetic and electric near-field coupling.

20 Claims, 3 Drawing Sheets

(51) Int. Cl.
*G08C 17/04* (2006.01)
*H04B 5/02* (2006.01)
*H04B 13/00* (2006.01)
*G08C 17/02* (2006.01)
*H02J 50/12* (2016.01)
*H02J 7/02* (2016.01)
*A61B 5/00* (2006.01)

(52) U.S. Cl.
CPC ............ *H02J 50/12* (2016.02); *H04B 5/0012* (2013.01); *H04B 5/0081* (2013.01); *H04B 5/0093* (2013.01); *H04B 5/02* (2013.01); *H04B 13/005* (2013.01); *A61B 5/002* (2013.01); *H02J 7/025* (2013.01)

(56) References Cited

U.S. PATENT DOCUMENTS

| | | | |
|---|---|---|---|
| 4,692,743 A | 9/1987 | Holden | |
| 5,673,054 A | 9/1997 | Hama | |
| 5,708,732 A | 1/1998 | Merhav et al. | |
| 5,907,522 A * | 5/1999 | Teodoridis | H01Q 1/273 |
| | | | 343/718 |
| 5,914,701 A | 6/1999 | Gersheneld | |
| 5,926,573 A | 7/1999 | Kim et al. | |
| 5,948,006 A * | 9/1999 | Mann | A61N 1/08 |
| | | | 128/903 |
| 6,104,913 A | 8/2000 | McAllister | |
| 6,211,799 B1 * | 4/2001 | Post | A61B 5/0028 |
| | | | 340/10.51 |
| 6,223,018 B1 | 4/2001 | Fukumoto et al. | |
| 6,275,737 B1 * | 8/2001 | Mann | A61N 1/08 |
| | | | 607/61 |
| 6,424,820 B1 | 7/2002 | Burdick et al. | |
| 6,754,472 B1 | 6/2004 | Williams | |
| 6,816,600 B1 | 11/2004 | Jakob | |
| 7,142,681 B2 | 11/2006 | Kortekaas | |
| 7,171,177 B2 | 1/2007 | Park et al. | |
| 7,206,423 B1 | 4/2007 | Feng et al. | |
| 7,254,246 B2 | 8/2007 | Jakob | |
| 7,509,092 B2 | 3/2009 | Ishibashi et al. | |
| 7,664,476 B2 | 2/2010 | Yanagida | |
| 7,684,769 B2 | 3/2010 | Song et al. | |
| 7,783,067 B1 | 8/2010 | Frerking | |
| 7,796,943 B2 | 9/2010 | Levan | |
| 7,907,057 B2 | 3/2011 | Schaffler et al. | |
| 8,005,547 B2 * | 8/2011 | Forsberg | A61N 1/3787 |
| | | | 607/33 |
| 8,237,622 B2 | 8/2012 | Furumura et al. | |
| 8,265,554 B2 | 9/2012 | Hwang | |
| 8,280,302 B2 | 10/2012 | Kubono | |
| 8,401,470 B2 | 3/2013 | Kroenstoel et al. | |
| 8,452,234 B2 | 5/2013 | Hasegawa et al. | |
| 8,509,689 B2 | 8/2013 | Nakamura et al. | |
| 8,526,879 B2 | 9/2013 | Kristiansen | |
| 8,606,177 B2 | 12/2013 | Hwang | |
| 8,644,542 B2 * | 2/2014 | Klemenz | H04R 25/554 |
| | | | 381/323 |
| 8,797,148 B2 | 8/2014 | Kato et al. | |
| 8,829,725 B2 * | 9/2014 | Urano | H02J 17/00 |
| | | | 307/104 |
| 8,878,735 B2 | 11/2014 | Kvist et al. | |
| 8,892,055 B2 | 11/2014 | Gasperi | |
| 8,909,966 B2 * | 12/2014 | Furukawa | H04B 5/0037 |
| | | | 323/211 |
| 9,019,131 B2 | 4/2015 | Kim | |
| 9,024,725 B2 | 5/2015 | Ikemoto | |
| 9,083,391 B2 | 7/2015 | Teggatz | |
| 9,130,273 B2 | 9/2015 | Kataoka | |
| 9,197,986 B1 | 11/2015 | Kerselaers et al. | |
| 9,314,381 B2 | 4/2016 | Curran et al. | |
| 9,455,771 B2 | 9/2016 | Dobyns | |
| 9,647,462 B2 | 5/2017 | Angst et al. | |
| 2002/0003503 A1 | 1/2002 | Justice | |
| 2002/0181579 A1 | 12/2002 | Vetro et al. | |
| 2004/0023216 A1 | 2/2004 | Lu et al. | |
| 2004/0027296 A1 | 2/2004 | Gerber | |
| 2004/0138723 A1 | 7/2004 | Malick et al. | |
| 2005/0058201 A1 | 3/2005 | Fernandes | |
| 2006/0008038 A1 | 1/2006 | Song et al. | |
| 2006/0114993 A1 | 6/2006 | Xiong et al. | |
| 2006/0134918 A1 | 6/2006 | Fuji et al. | |
| 2006/0215919 A1 | 9/2006 | Srinivasan | |
| 2006/0233258 A1 | 10/2006 | Holcomb | |
| 2006/0252371 A1 | 11/2006 | Toshiharu | |
| 2007/0058713 A1 | 3/2007 | Shen et al. | |
| 2007/0116308 A1 | 5/2007 | Zurek et al. | |
| 2007/0190940 A1 | 8/2007 | Lee et al. | |
| 2007/0291970 A1 | 12/2007 | Nikles | |
| 2008/0182517 A1 | 7/2008 | Rass | |
| 2008/0186241 A1 | 8/2008 | Christensen | |
| 2008/0261523 A1 | 10/2008 | Kubono et al. | |
| 2008/0262376 A1 | 10/2008 | Price | |
| 2008/0267436 A1 | 10/2008 | Kerselaers et al. | |
| 2009/0041241 A1 * | 2/2009 | Dobyns | H04B 5/0031 |
| | | | 380/252 |
| 2009/0067653 A1 | 3/2009 | Meskens et al. | |
| 2009/0202084 A1 | 8/2009 | Joeng et al. | |
| 2009/0238279 A1 | 9/2009 | Tu et al. | |
| 2009/0315787 A1 * | 12/2009 | Schatzle | H01Q 1/273 |
| | | | 343/702 |
| 2009/0322540 A1 | 12/2009 | Richardson et al. | |
| 2010/0036773 A1 | 2/2010 | Bennet | |
| 2010/0136905 A1 * | 6/2010 | Kristiansen | H04B 5/0075 |
| | | | 455/41.1 |
| 2010/0311326 A1 | 12/2010 | Klabunde et al. | |
| 2011/0029041 A1 | 2/2011 | Wiskerke | |
| 2011/0046730 A1 | 2/2011 | Meskens | |
| 2011/0137649 A1 | 6/2011 | Rasmussen | |
| 2011/0196452 A1 * | 8/2011 | Forsell | H02J 7/025 |
| | | | 607/60 |
| 2011/0248673 A1 * | 10/2011 | Aerts | H02J 7/025 |
| | | | 320/108 |
| 2011/0250837 A1 | 10/2011 | Hwang et al. | |
| 2011/0255702 A1 | 10/2011 | Jensen | |
| 2011/0300801 A1 * | 12/2011 | Kerselaers | H04B 5/0087 |
| | | | 455/41.1 |
| 2012/0032778 A1 | 2/2012 | Nakano et al. | |
| 2012/0306714 A1 | 12/2012 | Yosui et al. | |
| 2013/0002517 A1 | 1/2013 | Pascolini et al. | |
| 2013/0113662 A1 | 5/2013 | Kato et al. | |
| 2013/0148828 A1 * | 6/2013 | Fort | A61N 1/36032 |
| | | | 381/312 |
| 2013/0171933 A1 | 7/2013 | Rofougaran | |
| 2013/0278470 A1 | 10/2013 | Kataoka | |
| 2013/0308805 A1 * | 11/2013 | Ozden | H01Q 1/243 |
| | | | 381/315 |
| 2013/0339025 A1 | 12/2013 | Suhami | |
| 2014/0008446 A1 | 1/2014 | Carr | |
| 2014/0023216 A1 * | 1/2014 | Solum | H04R 25/554 |
| | | | 381/315 |
| 2014/0049440 A1 | 2/2014 | Ueki et al. | |
| 2014/0062212 A1 * | 3/2014 | Sun | H01F 38/14 |
| | | | 307/104 |
| 2014/0184462 A1 | 7/2014 | Kuniaki | |
| 2014/0213184 A1 | 7/2014 | Matsubara | |
| 2014/0241555 A1 * | 8/2014 | Terlizzi | H04B 5/0006 |
| | | | 381/315 |
| 2014/0315486 A1 | 10/2014 | Broyde et al. | |
| 2014/0320369 A1 | 10/2014 | Azenui et al. | |
| 2014/0340032 A1 * | 11/2014 | Curtis | H04B 5/0037 |
| | | | 320/108 |
| 2015/0001956 A1 * | 1/2015 | Saen | H04B 5/0037 |
| | | | 307/104 |
| 2015/0028690 A1 * | 1/2015 | Sako | H02J 3/005 |
| | | | 307/104 |
| 2015/0038075 A1 | 2/2015 | Kataoka | |
| 2015/0038864 A1 | 2/2015 | Kataoka et al. | |
| 2015/0048985 A1 | 2/2015 | Park et al. | |
| 2015/0061587 A1 * | 3/2015 | Bruechmann | H04B 5/0031 |
| | | | 320/108 |

(56) References Cited

U.S. PATENT DOCUMENTS

| | | | |
|---|---|---|---|
| 2015/0079902 A1* | 3/2015 | Dhayni | G06K 7/0008 455/41.1 |
| 2015/0092962 A1 | 4/2015 | Amento | |
| 2015/0097442 A1* | 4/2015 | Muurinen | H04B 5/0037 307/104 |
| 2015/0130465 A1 | 5/2015 | Wiggins et al. | |
| 2015/0318603 A1 | 11/2015 | Kerselaers et al. | |
| 2015/0318613 A1 | 11/2015 | Kerselaers et al. | |
| 2015/0318932 A1 | 11/2015 | Kerselaers et al. | |
| 2015/0319545 A1 | 11/2015 | Kerselaers et al. | |
| 2015/0351292 A1 | 12/2015 | Chang et al. | |
| 2016/0189860 A1 | 6/2016 | Konanur et al. | |
| 2017/0125833 A1 | 5/2017 | Tenno | |

FOREIGN PATENT DOCUMENTS

| | | |
|---|---|---|
| CN | 103024621 A1 | 4/2013 |
| KR | 101584555 B1 | 1/2016 |
| WO | WO 03/030991 A1 | 4/2003 |
| WO | WO03030991 A1 | 4/2003 |
| WO | WO2013183575 | 12/2013 |

OTHER PUBLICATIONS

Zimmerman, Personal Area Networks: Near Field IntraBody Communication, IBM System Journal, vol. 35, 1995, pp. 609-617.*

Kado, et al., "RedTacton Near-body Electric-field Communications Technology and Its Applications", NTT Technical Review, vol. 8, No. 3; NTT Microsystems Integration Laboratories, Atsugi-shi, JP;, Mar. 2010, pp. 1-6.

EP COMM and Search Report for EP 15164621 dated Aug. 31, 2015.

Cho, et al., A Planar MICS Band Antenna Combined with a Body Channel Communication Electrode for Body Sensor Network, IEEE Transactions on Microwave Theory and Technique, IEEE Service Center vol. 57, No. 10, Oct. 1, 2009.

Shinagawa, et al., A Near-Field Sensing Transceiver for Intra-Body Communication Based on a Electro-Optic Effect, IMTC 2003, Proceedings of the 20th, IEEE Instrumentation and Measurement Technology Conference, May 20-22, 2003, vol. 1&2, pp. 296-301.

Ohishi, et al., Novel Pair Electrode With Coils Sensing Magnetic Energy on Human Body Surface for Intrabody Communication, Antennas and Propagation (ISAP) 2012 Int'l. Symposium on, IEEE, Oct. 29, 2012, pp. 203-206.

Zimmerman, Personal Area Networks: Near-Field Intrabody Communication IBM Systems Journal, vol. 35, No. 3-4, Jan. 1996, pp. 609-617.

Non Final Office Action dated Aug. 26, 2016 for U.S. Appl. No. 14/270,013, 13 pages.

Non-Final Office Action for U.S. Appl. No. 14/576,583, Nov. 3, 2016, 33 pages.

Non-Final Office Action dated Jan. 3, 2017 for U.S. Appl. No. 14/576,030, 39 pages.

Final Office Action dated Aug. 27, 2015 for U.S. Appl. No. 14/270,013, 17 pages.

International Search Report and Written Opinion dated July 13, 2015 for PCT/EP2015/058044, 11 pages.

Non-Final Office Action dated Feb. 29, 2016 for U.S. Appl. No. 14/270,013, 11 pages.

Non-Final Office Action dated May 7, 2015 for U.S. Appl. No. 14/270,013, 12 pages.

International Search Report and Written Opinion dated Jul. 17, 2015 for PCT/EP2015/058052, 9 pages.

Notice of Allowance dated Jul. 21, 2015 for U.S. Appl. No. 14/302,791, 9 pages.

International Search Report and Written Opinion dated Jul. 7, 2015 for PCT/EP2015/058071, 11 pages.

U.S. Appl. No. 14/551,988, filed Nov. 24, 2014, entitled "Electromagnetic Field Induction for Inter-Body and Transverse Body Communication".

European Search Report dated Aug. 31, 2015 for EP 15164678, 6 pages.

Final Office Action dated Mar. 7, 2016 for U.S. Appl. No. 14/576,030, 13 pages.

Non-Final Office Action dated Oct. 5, 2015 for U.S. Appl. No. 14/576,030, 17 pages.

European Search Report dated Aug. 31, 2015 for EP 15164622, 6 pages.

Final Office Action dated Feb. 25, 2016 for U.S. Appl. No. 14/576,583, 13 pages.

Non-Final Office Action dated Sep. 21, 2015 for U.S. Appl. No. 14/576,583, 17 pages.

Non-Final Office Action dated Oct. 5, 2015 for U.S. Appl. No. 14/575,865, 17 pages.

Final Office Action dated Mar. 4, 2016 for U.S. Appl. No. 14/575,865, 14 pages.

European Search Report dated Aug. 31, 2015 for EP 15164610, 6 pages.

U.S. Appl. No. 14/836,681, filed Aug. 26, 2015, entitled "Antenna System".

U.S. Appl. No. 15/146,665, filed May 4, 2016, entitled "Near-Field Electromagnetic Induction (NFEMI) Antenna".

Chandrasekar, K., "Inductively Coupled Connectors and Sockets for Multi-Gb/s Pulse Signaling," IEEE Transactions on Advanced Packaging, vol. 31, No. 4; Nov. 1, 2008, pp. 749-758.

Tounsi, F. et al. "Electromagnetic Modeling of an Integrated Micromachined Inductive Microphone," IEEE 4th International Conference on Design and Technology of Integrated Systems in Nanoscale Era; Apr. 6, 2009; pp. 38-43.

Zimmerman, T.G., "Personal Area Networks (PAN): Near-Field Intra-Body Communication," Massachusetts Institute of Technology, Jun. 1995, 81 pages.

Non Final Office Action dated Jun. 29, 2016 for U.S. Appl. No. 14/551,988, 23 pages.

Notice of Allowance dated Jun. 7, 2017 for U.S. Appl. No. 14/551,988, 25 pages.

Notice of Allowance dated Jun. 14, 2017 for U.S. Appl. No. 14/836,681, 14 pages.

Final Office Action dated Mar. 14, 2017 for U.S. Appl. No. 14/270,013, 37 pages.

Notice of Allowance dated Jun. 27, 2017 for U.S. Appl. No. 14/576,030, 30 pages.

Notice of Allowance dated Jun. 21, 2017 for U.S. Appl. No. 14/576,583, 34 pages.

Final Office Action dated Jul. 27, 2017 for U.S. Appl. No. 14/575,865, 56 pages.

Non-Final Office Action dated Jan. 19, 2017 for U.S. Appl. No. 14/575,865, 45 pages.

Non-Final Office Action dated Jan. 19, 2017 for U.S. Appl. No. 14/551,988, 21 pages.

Non-Final Office Action dated Dec. 7, 2017 for U.S. Appl. No. 14/270,013, 41 pages.

Notice of Allowance dated Mar. 22, 2018 for U.S. Appl. No. 14/575,865, 24 pages.

Notice of Allowance dated Apr. 25, 2018 for U.S. Appl. No. 14/270,013, 19 pages.

Non Final Office Action dated May 24, 2018 for U.S. Appl. No. 15/146,665, 96 pages.

* cited by examiner

WIRELESS POWER DELIVERY AND DATA LINK

This application is a continuation-in-part of application Ser. No. 14/270,013, filed on May 5, 2014, which is hereby incorporated by reference for all purposes as if fully set forth herein. This application is also a continuation-in-part of application Ser. No. 14/302,791, filed on Jun. 12, 2014, which is hereby incorporated by reference for all purposes as if fully set forth herein.

TECHNICAL FIELD

Various example embodiments disclosed herein relate generally to wireless power and data delivery in close proximity to a living body.

BACKGROUND

There exist a variety of wireless power and data link systems which, illustratively, use electrostatic coupling as wireless transmission. Some systems are used for power and data links around the human body; other systems may be used for links in or around other objects. A wireless power transmitter usually operates at low frequencies in the sub MHz range. The transmitter generates an electrostatic field between the body and the environment that is referenced to the ground. A receiver at another position of the body can convert the electrostatic field to a voltage and power. Other applications around the human body operate at higher frequencies. For example, currently RF based hearing aids are considered for wireless communication. Often such hearing aid systems operate in the 2.5 GHz ISM band. Such systems feature propagation by means of transverse waves, the magnetic and electric fields being in phase and covering a relatively large range of perhaps 30 meters. The large range may cause problems in terms of security of the communication content and may cause interference. Furthermore, because of their relatively high frequency of operation, such systems are heavily influenced by the human body; for example, the delivery of sufficient power is very dependent on movements of the human body and allocation of the device.

SUMMARY

A brief summary of various example embodiments is presented below. Some simplifications and omissions may be made in the following summary, which is intended to highlight and introduce some aspects of the various embodiments, but not to limit the scope of the invention. Detailed descriptions of an example embodiment adequate to allow those of ordinary skill in the art to make and use the inventive concepts will follow in later sections.

Various embodiments relate to an electromagnetic induction wireless transceiver including a magnetic antenna; an electric antenna including first and second plates, the first plate being connectable to a body; and a power driver configured to produce a modulating signal used to drive the magnetic antenna and the electric antenna to produce electromagnetic induction fields, where the transceiver when connected to a body in a first location is configured to transmit power to a second electromagnetic induction wireless transceiver connected to a second location a distance from the first location, where the first and second locations are connected through magnetic and electric near-field coupling. In alternative embodiments the second electromagnetic induction wireless transceiver is connected to a second body through electric and magnetic near field coupling with the first body. Other embodiments further include an energy source connected to the power driver. In alternative embodiments the energy source includes one of a battery, a solar energy collector, or a kinetic energy collector.

Some embodiments further include an adaptable matching unit connected to the power driver. In further embodiments the adaptable matching unit includes an interface to the antennas. In alternative embodiments the adaptable matching unit conjugate matches the power driver and the antennas. Some embodiments further include a radio unit connected to the electric antenna and the magnetic antenna. Other embodiments further include a music source device including the electromagnetic induction wireless transceiver. Further embodiments include a wireless speaker device including the second electromagnetic induction wireless transceiver. In some embodiments, the wireless speaker device includes earbuds.

Various embodiments relate to an electromagnetic induction wireless transceiver including a magnetic antenna configured to receive an electromagnetic induction field; an electric antenna configured to receive the electromagnetic induction field including first and second plates, the first plate being connectable to a body; and a receiver configured to receive a modulating signal carried by the electromagnetic induction fields, where the transceiver when connected to a body in a first location is configured to receive power from a second electromagnetic induction wireless transceiver connected to a second location a distance from the first location, where the first and second locations are connected through magnetic and electric near-field coupling. Further embodiments include a tuning circuit configured to tune an antenna combination, where the antenna combination includes the magnetic antenna and the electric antenna. Further embodiments include a controller including a data processing unit and signal processing unit, where the controller controls the operation of the receiver. Some embodiments include a wireless speaker device coupled to the transceiver. In some embodiments the wireless speaker device includes earbuds. Some embodiments further include a music source device coupled to the second electromagnetic induction wireless transceiver.

Various embodiments relate to a method of communicating between devices near bodies including producing a communication signal by a first device connected to a first body; and applying the communication signal to a magnetic antenna and an electric antenna in the first device to produce electromagnetic induction fields, where the electromagnetic induction fields are capable of being received by a second device connected to a second body such that the first device communicates with the second device, where the first and second bodies are connected through magnetic and electric near-field coupling.

Various embodiments relate to a method of transferring data and power between devices near bodies including producing a communication signal by a first device connected to a first body; producing a modified communication signal, where the modified communication signal has one of an amplitude difference, phase difference, and an amplitude and phase difference from the communication signal; applying the communication signal to one of a magnetic antenna and an electric antenna; applying the modified communication signal to the other of the magnetic antenna and the electric antenna, where applying the communication signal and the modified communication signal to the magnetic and electric antennas produces electromagnetic induction fields and where the electromagnetic induction fields are capable of being received by a second device connected to the second body such that the first device communicates with the second device, where the first and second bodies are connected through magnetic and electric near-field coupling; and controlling the production of the modified communication signal to improve the method of transferring data and power between the first and second devices.

Various embodiments relate to a method of communicating between inside and outside of a living body including producing a communication signal by a first device inside a living body; and applying the communication signal to a magnetic antenna and an electric antenna in the first device to produce electromagnetic induction fields, where the electromagnetic induction fields are capable of being received by a second device connected to the outside of the same living body such that the first device communicates with the second device.

Various embodiments relate to a method of communicating between inside and outside of a living body, including producing a communication signal by a first device inside a living body; and producing a modified communication signal, where the modified communication signal has one of an amplitude difference, phase difference, and an amplitude and phase difference from the communication signal; applying the communication signal to one of a magnetic antenna and an electric antenna; applying the modified communication signal to the other of the magnetic antenna and the electric antenna, where applying the communication signal and the modified communication signal to the magnetic and electric antennas produces electromagnetic induction fields and where the electromagnetic induction fields are capable of being received by a second device connected to the outside of the same living body such that the first device communicates with the second device; and controlling the production of the modified communication signal to improve the method of communicating between the first and second devices. Some embodiments further include tuning the antenna combination, where the antenna combination includes the electric antenna and the magnetic antenna. In alternative embodiments tuning the antenna combination includes varying the capacitance of a tuning capacitor coupled to the antenna combination, where the antenna combination includes the electric antenna and the magnetic antenna. Some embodiments further include monitoring signals at the magnetic antenna and the electric antenna; and adjusting the modified communication signal based upon the monitored signals.

BRIEF DESCRIPTION OF THE DRAWINGS

In order to better understand various embodiments, reference is made to the accompanying drawings, wherein.

To facilitate understanding, identical reference numerals have been used to designate elements having substantially the same or similar structure and/or substantially the same or similar function.

DETAILED DESCRIPTION

Figure 1:
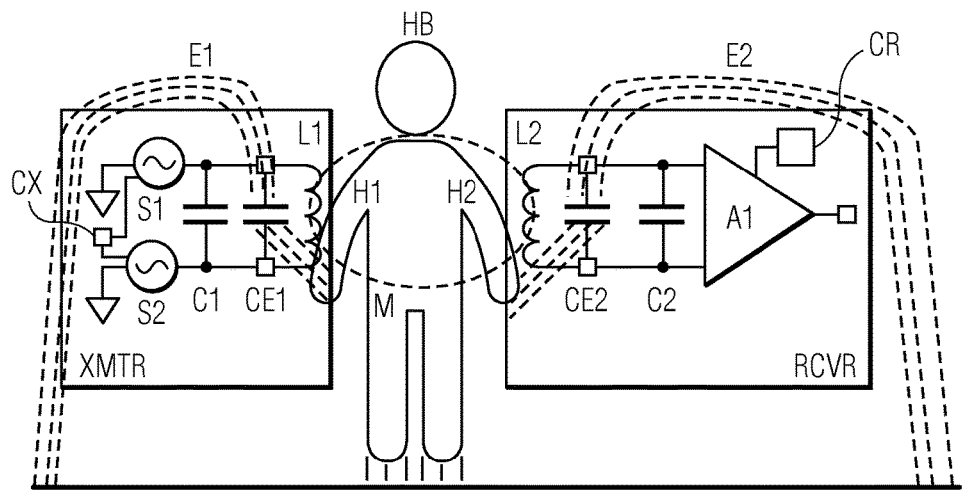
FIG. 1 illustrates a block diagram of wireless communication system.

The description and drawings illustrate the principles of the invention. It will thus be appreciated that those skilled in the art will be able to devise various arrangements that, although not explicitly described or shown herein, embody the principles of the invention and are included within its scope. Furthermore, all examples recited herein are principally intended expressly to be for pedagogical purposes to aid the reader in understanding the principles of the invention and the concepts contributed by the inventor(s) to furthering the art, and are to be construed as being without limitation to such specifically recited examples and conditions. Additionally, the term, "or," as used herein, refers to a non-exclusive or (i.e., and/or), unless otherwise indicated (e.g., "or else" or "or in the alternative"). Also, the various embodiments described herein are not necessarily mutually exclusive, as some embodiments can be combined with one or more other embodiments to form new embodiments. As used herein, the terms "context" and "context object" will be understood to be synonymous, unless otherwise indicated.

The link budget of an electromagnetic induction radio may be defined as, $$\text{Link Budget [dB]} = 20\ \text{log}10\left(\frac{V_{Rx}}{V_{Tx}}\right),$$

where $V_{Tx}$ is the transmitter voltage on the transmitter antennas and $V_{Rx}$ is the received voltage on the receiver antennas. In a related U.S. patent application Ser. No. 14/270,013 entitled "ELECTROMAGNETIC INDUCTION FIELD COMMUNICATION" filed on May 5, 2014 an electromagnetic communication method near a living body by means of a combination of a magnetic field and electric field with no intention to form transversal radiating waves is described. This results in a method that improves the link budget and extends the range to the complete living body and enables communication between devices near living bodies, including a first device connected to a first body and a second device connected to a second body such that the first device communicates with the second device, wherein the first and second bodies are connected through magnetic and electric near-field coupling. Even communication between more than two bodies is possible, but the embodiments described herein will use two living bodies for simplicity. Multiple devices with transceivers are also possible, but the embodiments described herein will use two devices or transceivers for simplicity.

The magnetic field is generated by a current through a first coil. The electric field may be generated by a first coupling capacitor, having a first conducting plate coupled to the body and a second conducting plate coupled to the environment. The wireless communication system is not galvanically connected to the ground. The magnetic and electric field may be received by a receiver at another place near the body by means of a second coil and a second coupling capacitor, the second capacitor having a first conducting plate coupled to the body and a second conducting plate coupled to the environment.

Figure 2:
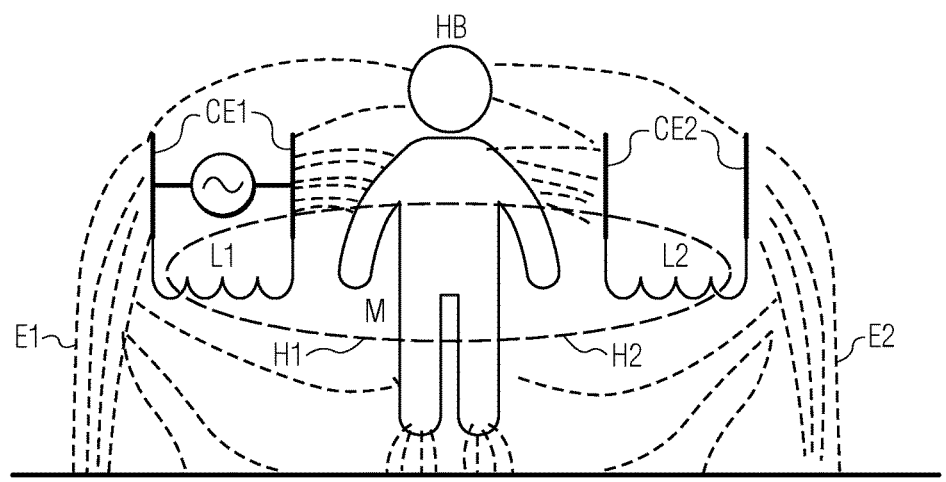
FIG. 2 illustrates a diagram of electrical and magnetic field lines during operation of the wireless communication system.

FIG. 1 illustrates a block diagram of a wireless communication system. FIG. 2 illustrates a diagram of electrical and magnetic field lines during operation of a wireless communication and power transfer system. The wireless communication system of FIG. 1 includes a transmitter XMTR and receiver RCVR. Communication between transmitter XMTR and receiver RCVR is accomplished via a combination of an electric field and a magnetic field as will be further described. The transmitter XMTR and receiver RCVR are spaced apart from the human body HB by an exaggerated distance so that the electric field may be shown. The human body may be replaced by any other living body in FIG. 1 and FIG. 2. Magnetic field H1 is generated by current through coil L1. An electric field E1 can be generated by a voltage on coupling capacitor CE1. Coupling capacitor CE1 has a first conducting plate coupled to the human body HB and a second conducting plate coupled to the environment as will be further illustrated below. Capacitors C1 and C2 are provided to resonate their respective circuits at the required operational frequency.

Magnetic field H1 and electric field E1 may be generated by the same voltage using sources S1 and S2. Accordingly, the sources S1 and S2 produce the communication signal to be transmitted. In this illustrative embodiment the sources S1 and S2 may generate a balanced voltage across the coil L1. However the voltage across the coil L1 may also be unbalanced and in this case only one source is required.

Magnetic field H2 and electric field E2 (which have different amplitudes than magnetic field H1 and electric field E1 respectively) may be received at a receiver RCVR positioned at another place near the human body (perhaps in the other ear) by means of a coil L2 and a coupling capacitor CE2. Coupling capacitor CE2 has a first conducting plate coupled to the human body HB and a second conducting plate coupled to the environment. Further, coils L1 and L2 may have a mutual inductance M.

FIG. 1 shows an illustrative embodiment of a transmitter XMTR and receiver RCVR that allows uni-directional communication. In another embodiment, both XMTR and RCVR may be also transceivers and bi-directional communication is thus made possible.

Not illustrated in detail are driving circuitry, signal processing circuitry, microphones, control circuitry, etc., although such items may be viewed as embodied in blocks denoted by CX or CR in FIG. 1.

This wireless communication system communicates using a wireless electromagnetic field communication method near a human body. The electromagnetic induction fields are a combination of a magnetic field H1 and electric field E1 with no intention to form transversal radiating waves. The magnetic field H1 is generated by a magnetic antenna, a coil L1, while the electric field E1 is generated by a voltage on a coupling capacitor CE1. By using two antennas, one predominantly sensitive to the magnetic field and the second predominantly sensitive to the electric field, magnetic and electric induction fields may be transmitted close to the human body that can be received at another place at the body. The signals from both antennas may be combined in an efficient way to establish a communication link budget that is superior to those of prior art magnetic induction (MI) methods.

The coil L1 may be positioned close to the human body HB and may make skin contact or not. The coil L1 that generates magnetic field H2 also generates an electric field. The wireless system, including the transmitter XMTR and receiver RCVR, is not galvanically connected to the ground. It will be noted that the electric field lines E1 and E2 extend down the length of the human body HB.

A combination of magnetic field and electric field is created, and the electric field is present between the living body and the environment. The magnetic induction field decreases with 60 db per decade distance from the source in air, however the electric induction field decreases with less than 60 db per decade distance from the source.

The magnetic field H2 and electric field E2 can be received by a receiver at another place near the human body by means of a coil L2 and a coupling capacitor CE2. An electric source drives a current through antenna coil L1, generating a magnetic field that is passed through the body HB with the same attenuation as in air because the magnetic permeability, μ, is the same for the bio material in human body as it is for air. The magnetic field will be attenuated with the 3th power of the distance. The human body HB may be positioned on a floor F which may be conductive or not.

The orientation of the electric field E1 may be normal to the human body skin. The electric field E1 may be measured on the whole body and is strongest near the capacitor CE1. The electric field may be attenuated with less than 60 db per decade distance from the capacitor CE1. However the irregular shape of the body along a transmission path may give extra attenuation. This is different compared with a transmission path in air where the electric field is attenuated with the 3th power of the distance (an attenuation of 60 db per decade distance from the antenna).

In the embodiments discussed, the coils and coupling capacitors are so small (i.e. less than about 5% of the wavelength of the electric E1 and E2 and magnetic H1 and H2 fields), that there is not significant generation of undesired transverse radiating waves.

In an embodiment, coils L1 and L2 are unscreened and smaller (ideally much smaller) than the chosen wavelength of operation.

Figure 3:
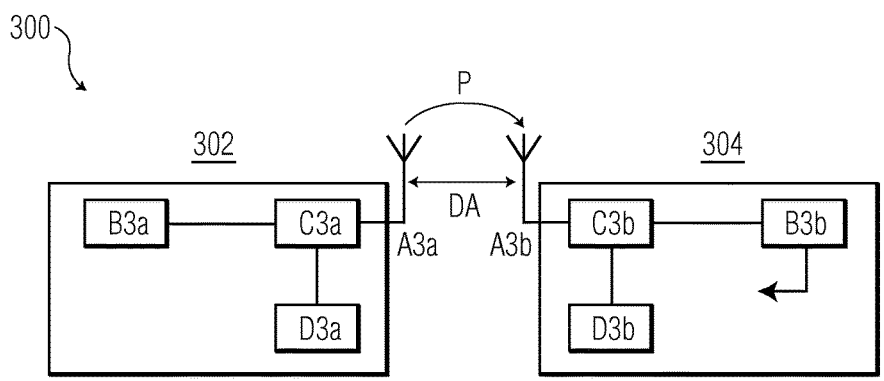
FIG. 3 illustrates a block diagram of a wireless power delivery and data link.

In addition to data communication, power may be transferred wirelessly along a human body HB. FIG. 3 illustrates a block diagram 300 of an embodiment of a transceiver 302 and a transceiver 304 that may wirelessly transmit and receive simultaneous power and data. Transceiver 302 and transceiver 304 may be attached to a human body HB. In some embodiments, transceiver 302 may transmit data by modulating a carrier from which power is derived. Any modulation scheme may be used. In some embodiments, other methods of communication may be used.

In some embodiments, transceiver 302 and/or transceiver 304 may be physically displaced from the human body such as body HB, provided that both transceivers are close enough to the human body to be coupled so that power and data are transmitted through a combination of electric and magnetic fields.

Transceiver 302 may contain a unit B3a to convert power from an external source to a low frequency power signal. The external source may include one or more sources such as for example a battery, a solar energy collector, or a vibrational device that collects kinetic energy; these energy sources may be driven by a wearer's own movement or energy. Unit B3a may include a power driver. Unit B3a may drive unit C3a. Unit C3a may include an adaptable matching unit and interface to an antenna A3a. Unit C3a may include matching components to conjugate match the output impedance of unit B3a with the antenna A3a input impedance so that maximum power may be delivered to the antenna A3a. Unit C3a may also transmit data by modulating the power signal. Antenna A3a may generate a combined electric and magnetic field around the human body as described above.

Transceiver 302 may also include an additional Unit D3a with additional functions to perform as a complete radio as known in the art.

Transceiver 304 may be placed at a position apart from transceiver 302 on a human body such as body HB. Transceiver 304 may include an antenna A3b capable of receiving a combination of electric and magnetic fields and converting it to an electric signal. Unit C3b may contain an interface to antenna A3b and an adaptable matching network to conjugate match the antenna impedance. A received signal may be converted to DC power in unit B3b. In some embodiments, an electrically signal sensitive switch may start powering the transceiver 304. Such a mechanism may save power when transceiver 304 is inactive. Transceiver 304 may be powered by the received signal from another transceiver such as transceiver 302. When transceiver 304 is active and powered, unit D3b may demodulate data received from the powering transceiver such as transceiver 302. Unit D3b may also include additional functions to function as a radio as known in the art. Although two transceivers are discussed, in some embodiments more than two transceivers may be configured in a network across a body such as body HB.

In some embodiments, Antennas A3a and/or A3b may measure 2 cm$^2$. In some embodiments, a frequency of 10 MHz may be used for power and/or data transmission between a transceiver such as transceiver 302 and another transceiver such as transceiver 304. The transmission frequency of 10 MHz has a wavelength of 30 meters, much larger compared to the size of antennas A3a and A3b. In some embodiments, power and data may be transferred along a human body, or between two or more bodies through physical contact, by using bodies as a medium for signal propagation.

The combination of electric and magnetic induction fields significantly improves power transmission across a human body when compared to electrostatic induction. Power loss as a function of the distance from the transmission point to the receiver when wirelessly transmitted across a human body such as human body HB depends on a combination of the electrical and magnetic fields, where the rate of energy transfer per unit area (power density) is the product of the electric field strength (E) times the magnetic field strength (H). The E/H ratio is not constant but varies with a specific distance from the generating device. Further, the E/H ratio is function of the transmitter antenna and applied power.

Figure 4:
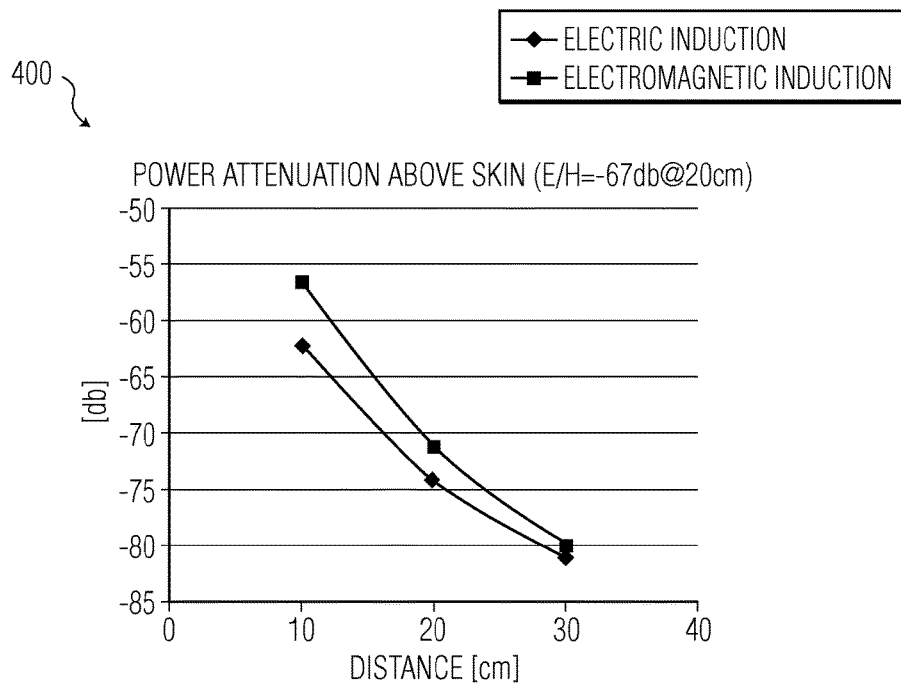
FIG. 4 is a diagram illustrating comparative ranges of a wireless power system which uses electrostatic field induction and a wireless power system using electromagnetic field induction.

As an example, FIG. 4 illustrates an example power attenuation 400 simulated on a human body model including 3 layers, a 2 mm skin layer, a 2 mm fat layer, and a 8 mm muscle layer, taken from the Bio-tissue database of a 3-dimensional electromagnetic field simulator of CST Microwave Studio. As shown, the simulation has an E/H ratio of −67 db measured at 20 cm distance from the source antenna. The transmitter and receiver antennas may include a ferrite coil 9 mm long with a diameter of 2 mm, combined with a coupling capacitor including 20 by 20 mm conducting plates separated by 5 mm of air. The results shown in the example of FIG. 4 may be achieved by an antenna positioned 2 mm from the simulated human body. As shown in FIG. 4, at 10 cm distance from the transmitting antenna, power loss is 5.5 db less when electric and magnetic fields are used in combination to create electromagnetic induction, than when electric induction using only an electrostatic field is used.

In another example, a power transmitting node with a transmitter antenna which may generate an electric and magnetic induction field at 10.6 MHz may be configured with a planar coil of 5 windings, 50 mm by 35 mm, combined with a coupling capacitor including 45 by 30 mm conducting plates separated by 1 mm of air and may be positioned close to a human body with the antenna 2 mm from the wrist. A receiver may be positioned 2 mm from the body near the chest, and may include a ferrite coil 9 mm long with a diameter of 2 mm, combined with a coupling capacitor including 15 by 10 mm conducting plates separated by 4 mm of air. On a live human body, using an electromagnetic induction field, the power loss between a transmitter at the wrist position and a second receiving node at the chest as described above may be 41 db, an improvement of 8 db over electrostatic induction. In another example, where the electromagnetic power transmitting node is placed 2 mm from a foot, the power loss between the foot position and a second receiving node at the chest of a human is 37.8 db, an improvement over electrostatic transmission of 5.7 db in power.

As such, power and data may be efficiently distributed across a body. For example, intra-body power distribution may be used in a body area network of passive patches that are powered remotely by a central device such as a watch. In another example, devices may be displaced from the body but still coupled enough to the body's electromagnetic field to be powered or to power other passive devices. Inter-body power distribution and data communication may be triggered, for example, by shaking hands, for instance, activating and communicating with a receiver positioned about another person.

In another example, electromagnetic induction between a transmitter such as transmitter 302 and a receiver such as receiver 304 may be used to transmit data and power between two or three devices. For example, an electromagnetic induction (EMI) transmission may transfer both communication and power between a music source device, for example, a mobile device or mp3 player and wireless speakers, for example, earbuds, as opposed to transferring audio but not power. Note that remote speakers may require relatively little power; for example only a few mW or lower may be required for audio processing and a speaker driver—thus even 1% efficiency in power transmission from the source device would be acceptable where the external device has substantial battery capacity relative to the needs of the speaker.

In such an example arrangement the remote speakers may not include a battery because all processing and speaker driver functionality may be powered by transferring the power from the remote device to the remote speakers. In an example arrangement where batteries are not required the remote speakers may be smaller, lighter and include less expensive components; further, the need to periodically recharge the remote speakers may be eliminated.

Further, electromagnetic induction may provide a link budget up to −30 dB for on-body communication, ensuring successful audio reception at both ears, provided the source device is worn on or close to the body; for instance, electromagnetic induction may only provide good link budget when both devices are on or close to the body, such that electromagnetic induction based audio streaming may not be feasible from a device that is, for example, a meter away from the user.

Figure 5:
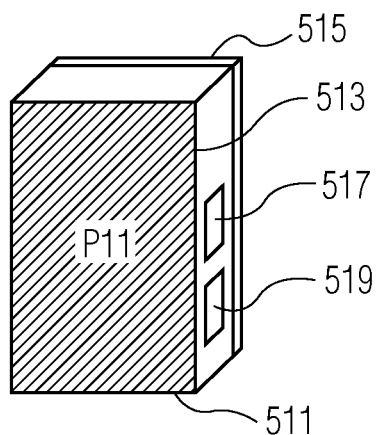
FIG. 5 depicts a control and/or display unit.

In another embodiment, there may be a separate control and/or display unit. FIG. 5 depicts a control and/or display unit 511. Control and/or display unit 511 has two plates 513 and 515 on opposite sides that function as the coupling capacitor CE1. Control and/or display unit 511 may be held in the hand of a user. One of the plates, 513 or 515 will be held more securely in the hand than the other and will therefore be more strongly coupled to the user's body, while the other plate will have a somewhat stronger coupling to the environment. Control and/or display unit 511 is capable of communicating with transmitter XMTR or receiver RCVR. Illustratively, control and/or display unit may, in combination, or individually, provide: volume control; noise reduction control; human body parameters such as heart rate, and other items such as physical parameters monitored around the body. Operation of the control and/or display unit is facilitated by the electromagnetic induction fields. In an embodiment, dimensioning and parallelism of the plates 513 and 515 of coupling capacitor CE1 are similar to that described above. Control and/or display unit may have a display 517, and internal circuitry, 519, similar to either transmitter XMTR or receiver RCVR (or may have internal circuitry which is a transceiver as previously described).

Although various embodiments described relate to a method of communicating near a living body, propagating near objects other than a living body may be used in the described embodiments. The first and a second device may be connected through magnetic and electric near-field coupling using the objects to help propagate the fields.

It should be appreciated by those skilled in the art that any block diagrams herein represent conceptual views of illustrative circuitry embodying the principles of the invention. Further, in the circuits shown additional elements may also be included as needed, or variations to the structure of the circuit may be made to achieve the same functional results as the circuits illustrated.

Although the various example embodiments have been described in detail with particular reference to certain aspects thereof, it should be understood that the invention is capable of other embodiments and its details are capable of modifications in various obvious respects. As is readily apparent to those skilled in the art, variations and modifications can be effected while remaining within the spirit and scope of the invention. Accordingly, the foregoing disclosure, description, and figures are for illustrative purposes only and do not in any way limit the invention, which is defined only by the claims.

What is claimed is:

1. An electromagnetic induction wireless transceiver system comprising: a transceiver comprising:
   a magnetic antenna comprising a coil;
   an electric antenna comprising a capacitor connected in parallel with the coil, the capacitor including first and second plates, the first plate being coupled to a living body; and
   a power driver configured to produce a modulating power signal according to data to be transmitted, the modulating power signal used to drive the magnetic antenna to produce a near-field magnetic field and to drive the electric antenna to produce a near-field electric field, wherein the near-field electric field is coupled to the living body and is available around the living body, and the near-field electric field has a direction normal to a surface of the living body,
   wherein the transceiver, when coupled to the living body in a first location, is configured to transmit, via the near-field magnetic field and the near-field electric field, the modulating power signal that simultaneously conveys the data and power to a second electromagnetic induction wireless transceiver coupled to the living body at a second location distant from the first location,
   wherein the modulating power signal is converted to direct current (DC) power to operate the second electromagnetic induction wireless transceiver.

2. The electromagnetic induction wireless transceiver system of claim 1, wherein the second electromagnetic induction wireless transceiver is connected to a second body through electric and magnetic near field coupling with the first body.

3. The electromagnetic induction wireless transceiver system of claim 1, further comprising an energy source connected to the power driver.

4. The electromagnetic induction wireless transceiver system of claim 3, wherein the energy source comprises one of a battery, a solar energy collector, or a kinetic energy collector.

5. The electromagnetic induction wireless transceiver system of claim 1, further comprising an adaptable matching unit connected to the power driver.

6. The electromagnetic induction wireless transceiver system of claim 5, wherein the adaptable matching unit comprises an interface to the antennas.

7. The electromagnetic induction wireless transceiver system of claim 5, wherein the adaptable matching unit conjugate matches the power driver and the antennas.

8. The electromagnetic induction wireless transceiver system of claim 1, further comprising:
   a radio unit connected to the electric antenna and the magnetic antenna.

9. The electromagnetic induction wireless transceiver system of claim 1, further comprising:
   a music source device comprising the electromagnetic induction wireless transceiver.

10. The electromagnetic induction wireless transceiver system of claim 9, further comprising:
    a wireless speaker device comprising the second electromagnetic induction wireless transceiver.

11. The electromagnetic induction wireless transceiver system of claim 10, wherein the wireless speaker device comprises earbuds.

12. The electromagnetic induction wireless transceiver system of claim 1, wherein a rate of energy transfer per unit area for transmitting the power to the second electromagnetic induction wireless transceiver is a product of an electric field strength times a magnetic field strength, wherein a ratio of the electric field strength to the magnetic field strength at the second location varies as a distance from the first location to the second location and is a function of an amount of power applied by the power driver.

13. The electromagnetic induction wireless transceiver system of claim 1, wherein the second electromagnetic induction wireless transceiver comprises a second magnetic antenna configured to receive the near-field magnetic field, a second electric antenna configured to receive the near-field electric field, wherein the near-field magnetic field passes through the living body, and the near-field electric antenna comprises a capacitor including third and fourth plates, the third plate coupled to the living body.

14. An electromagnetic induction wireless transceiver comprising:
    a magnetic antenna comprising a coil configured to receive near-field magnetic field;
    an electric antenna comprising a capacitor connected in parallel with the coil, the capacitor including first and second plates, the first plate being coupled to a living body; and
    a receiver configured to receive a modulating power signal carried by a near-field magnetic field and a near-field electric field, wherein
       the transceiver, when coupled to the living body in a first location, is configured to receive, via the near-field magnetic field and the near-field electric field, the modulating power signal from a second electromagnetic induction wireless transceiver coupled to the living body in a second location a distance from the first location, the transceiver is configured to convert the modulating power signal into direct current (DC) power to operate the electromagnetic induction transceiver and to simultaneously demodulate data from the modulating power signal, and the near-field electric field is coupled to the living body and is available around the living body, and the near-field electric field has a direction normal to a surface of the living body.

15. The electromagnetic induction wireless transceiver of claim 14, further comprising:

a tuning circuit configured to tune an antenna combination, wherein the antenna combination comprises the magnetic antenna and the electric antenna.

16. The electromagnetic induction wireless transceiver of claim 14, further comprising:

a controller comprising a data processing unit and signal processing unit, wherein the controller is configured to control operation of the receiver.

17. The electromagnetic induction wireless transceiver of claim 14, further comprising:

a wireless speaker device coupled to the electromagnetic induction wireless transceiver.

18. The electromagnetic induction wireless transceiver of claim 17, wherein the wireless speaker device comprises earbuds.

19. The electromagnetic induction wireless transceiver of claim 14, further comprising:

a music source device coupled to the second electromagnetic induction wireless transceiver.

20. The electromagnetic induction wireless transceiver of claim 14, wherein a rate of energy transfer per unit area for receiving the power from the second electromagnetic induction wireless transceiver is a product of an electric field strength times a magnetic field strength, wherein a ratio of the electric field strength to the magnetic field strength at the first location varies as a distance from the second location to the first location and is a function of an amount of power applied at the second electromagnetic induction wireless transceiver.

* * * * *